United States Patent
Ferro et al.

(10) Patent No.: US 11,147,577 B2
(45) Date of Patent: Oct. 19, 2021

(54) COMBINATION DEVICE FOR ENDOSCOPIC AND ARTHROSCOPIC SURGICAL PROCEDURES

(71) Applicant: AOD Holdings, LLC, Arroyo Grande, CA (US)

(72) Inventors: Thomas D. Ferro, Arroyo Grande, CA (US); Joseph R. Phillips, Paso Robles, CA (US); Austin T. Ferro, San Luis Obispo, CA (US); Donald J. Lee, San Luis Obispo, CA (US)

(73) Assignee: Applied Orthopedic Design, Inc., Arroyo Grande, CA (US)

(*) Notice: Subject to any disclaimer, the term of this patent is extended or adjusted under 35 U.S.C. 154(b) by 269 days.

(21) Appl. No.: 16/517,445

(22) Filed: Jul. 19, 2019

(65) Prior Publication Data

US 2019/0336158 A1 Nov. 7, 2019

Related U.S. Application Data

(63) Continuation of application No. 15/090,470, filed on Apr. 4, 2016, now Pat. No. 10,398,459.

(60) Provisional application No. 62/142,009, filed on Apr. 2, 2015, provisional application No. 62/183,903, filed on Jun. 24, 2015.

(51) Int. Cl.
*A61B 17/295* (2006.01)
*A61B 17/16* (2006.01)
*A61B 90/00* (2016.01)
*A61B 17/00* (2006.01)

(52) U.S. Cl.
CPC ........ *A61B 17/295* (2013.01); *A61B 17/1608* (2013.01); *A61B 2017/00353* (2013.01); *A61B 2090/0817* (2016.02)

(58) Field of Classification Search
CPC .............. A61B 17/1608; A61B 17/295; A61B 2017/00353; A61B 2090/0817; A61B 17/32
See application file for complete search history.

(56) References Cited

U.S. PATENT DOCUMENTS

| | | |
|---|---|---|
| 5,147,373 A | 9/1992 | Ferzli |
| 5,312,391 A | 5/1994 | Wilk |
| 5,474,057 A | 12/1995 | Makower |
| 5,562,694 A | 10/1996 | Sauer |
| 5,797,936 A | 8/1998 | Kleihues |
| 5,827,323 A | 10/1998 | Klieman |
| 5,954,731 A | 9/1999 | Yoon |
| 6,066,102 A | 5/2000 | Townsend |

(Continued)

OTHER PUBLICATIONS

Ferro; U.S. Appl. No. 15/090,470, filed Apr. 4, 2016.

(Continued)

*Primary Examiner* — George J Ulsh
(74) *Attorney, Agent, or Firm* — Fitch, Even, Tabin & Flannery LLP

(57) ABSTRACT

A single-handed meniscal biter instrument for probing and resecting meniscal tissue. The instrument includes a main body configured to be held by one hand and a cutting mechanism coupled to the main body and configured to be operable by the same hand while held. The instrument also includes an extendable probe coupled to the main body, wherein the probe is configured to be independently operable by the same hand while being held.

17 Claims, 18 Drawing Sheets

(56) References Cited

U.S. PATENT DOCUMENTS

| | | |
|---|---|---|
| 7,367,976 B2 | 5/2008 | Lawes |
| 7,918,868 B2 | 4/2011 | Marshall |
| 8,444,657 B2 | 5/2013 | Saadat |
| 8,814,885 B2 | 8/2014 | Domingo |
| 8,876,842 B2 | 11/2014 | Marshall |
| 9,072,524 B2 * | 7/2015 | Heard ............... A61B 18/1445 |
| 2005/0197661 A1 | 9/2005 | Carrison |
| 2012/0239080 A1 | 9/2012 | Fan |
| 2012/0323227 A1 | 12/2012 | Wolf |
| 2013/0274548 A1 | 10/2013 | Fels |
| 2014/0005663 A1 | 1/2014 | Heard |
| 2014/0277108 A1 | 9/2014 | Renton |
| 2015/0045797 A1 | 2/2015 | Papangelou |

OTHER PUBLICATIONS

Smith and Nephew Products Catalog "ACUFEX and ACUFEX Pro Punches, Scissors, Graspers and Knives"; downloaded Mar. 7, 2016 from http://smith-nephew.com/global/assets/pdf/temp/j-2012_punches_scissors_copy-1).pdf; 19 pages.
USPTO; Examiner Interview Summary issued in U.S. Appl. No. 15/090,470 dated Mar. 6, 2019.
USPTO; Final Office Action issued in U.S. Appl. No. 15/090,470 dated Dec. 21, 2018.
USPTO; Non-Final Office Action issued in U.S. Appl. No. 15/090,470 dated Jun. 19, 2018.
USPTO; Notice of Allowance issued in U.S. Appl. No. 15/090,470 dated Apr. 8, 2019.
USPTO; Restriction Requirement issued in U.S. Appl. No. 15/090,470 dated Feb. 26, 2018.

* cited by examiner

COMBINATION DEVICE FOR ENDOSCOPIC AND ARTHROSCOPIC SURGICAL PROCEDURES

This application is a continuation application of U.S. patent application Ser. No. 15/090,470, entitled COMBINATION DEVICE FOR ENDOSCOPIC AND ARTHROSCOPIC SURGICAL PROCEDURES, filed Apr. 4, 2016, which claims the benefit of U.S. Provisional Application No. 62/142,009 entitled MENISCAL SCULPTOR, filed Apr. 2, 2015, both of which are incorporated in their entirety herein by reference.

This application is a continuation application of U.S. patent application Ser. No. 15/090,470, entitled COMBINATION DEVICE FOR ENDOSCOPIC AND ARTHROSCOPIC SURGICAL PROCEDURES, filed Apr. 4, 2016, which claims the benefit of U.S. Provisional Application No. 62/183,903 entitled COMBINATION DEVICE FOR ENDOSCOPIC AND ARTHROSCOPIC SURGICAL PROCEDURES, filed Jun. 24, 2015, both of which are incorporated in their entirety herein by reference.

BACKGROUND OF THE INVENTION

1. Field of the Invention

The present invention relates generally to surgical methods and apparatus, and more specifically to surgical methods and apparatus for repair of the meniscus.

2. Discussion of the Related Art

The menisci are pieces of cartilage located in the knee joint, between the top of the tibia and the bottom of the femur. A meniscus can be torn as the result of injury and/or accident. The menisci are crucial to a healthy and properly functioning knee. The menisci act as a bumper to stabilize the central position of the femur on the tibia throughout the range of motion of the knee under various stresses. A meniscus tears as a result of cumulative trauma to the circumferentially oriented deeper fiber layers. The constant trauma to the meniscus may result in multiple planes of tissue separation and the formation of "flap" tears. These loose flaps of the meniscus cause impingement to the knee joint and meniscal tear symptoms. Treatment for these degenerative tears is surgical resection (removal) of the unstable flap fragments.

Torn menisci tend to be found in the posterior aspect of the knee joint where they are difficult to access with traditional basket forceps (also referred to as punches or biters) and power meniscal shavers. Flaps can be visualized with blunt hooks, but tend to retract away from the biting of the meniscal baskets. Difficult access of the posterior menisci tears can risk injury to the surrounding articular cartilage.

Therefore there is a need for an arthroscopic instrument configured to allow delivery of meniscal tissue into the accessible portion of the joint while the resecting (biting) part of the instrument can be used to efficiently remove the damaged meniscal tissue while minimizing damage to the surrounding healthy tissue.

SUMMARY OF THE INVENTION

Several embodiments of the invention advantageously address the needs above as well as other needs by providing a single-handed device comprising: a main body configured to be held by one hand; a cutting mechanism coupled to the main body and configured to be operable by the same hand when held; and an extendable probe coupled to main body, wherein the probe is configured to be independently operable by the same hand when held.

In another embodiment, the invention can be characterized as a probe assembly, comprising: a housing configured to couple to a cutting mechanism; a probe at least partially housed within the housing; and a mechanism housed within the housing and configured to extend and retract the probe while the housing is coupled to the cutting mechanism.

In yet another embodiment, the invention can be characterized as a method of using a single-handed meniscal biter device comprising the steps of: retracting of a probe, the probe extending forward from a main body of the device, from a forward extended position by pulling rearward a retraction trigger coupled to the probe, the retraction trigger coupled to the main body; maintaining the probe in the retracted position by holding the retraction trigger in a rearward position; inserting the probe into tissue; rotating a finger loop trigger pivotally coupled to the main body, whereby a lower biter jaw coupled to the finger loop trigger is actuated with respect to an upper biter jaw fixedly coupled to a housing coupled to the main body and extending away from the main body, whereby rotation of the finger loop trigger results in one of opening and closing of a jaw formed by the lower biter jaw and the upper biter jaw.

BRIEF DESCRIPTION OF THE DRAWINGS

The above and other aspects, features and advantages of several embodiments of the present invention will be more apparent from the following more particular description thereof, presented in conjunction with the following drawings.

Figure 1:
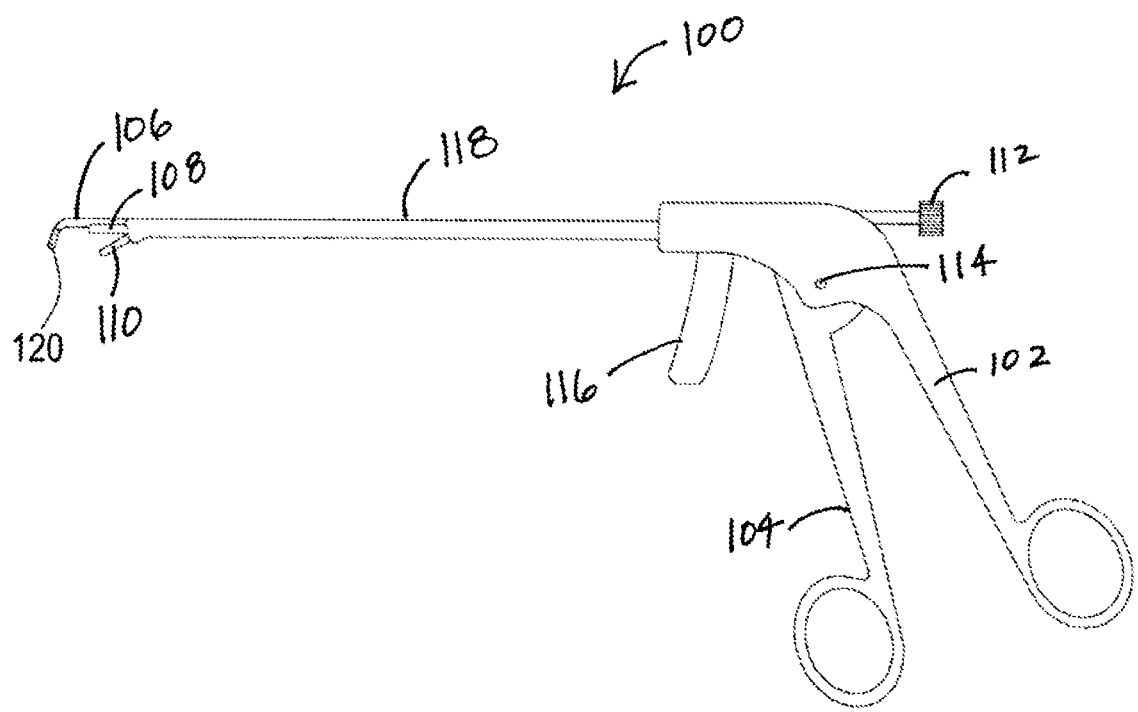
FIG. 1 is a side elevational view of a meniscal biter instrument in one embodiment of the present invention.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

DETAILED DESCRIPTION

The following description is not to be taken in a limiting sense, but is made merely for the purpose of describing the general principles of exemplary embodiments. The scope of the invention should be determined with reference to the claims.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided. One skilled in the relevant art will recognize, however, that the invention can be practiced without one or more of the specific details, or with other methods, components, materials, and so forth. In other instances, well-known structures, materials, or operations are not shown or described in detail to avoid obscuring aspects of the invention.

Referring first to FIG. 1, a side elevational view of a single-handed meniscal biter instrument 100 in one embodiment of the present invention is shown. Shown are a main body 102, a finger loop trigger 104, a probe 106, an upper biter jaw 108, a lower biter jaw 110, a dial 112, a pivot connection 114, a retraction trigger 116, and a housing 118.

The meniscal biter instrument 100 comprises the main body pivotally coupled to the finger loop trigger 104 at the pivot connection 114. The main body and the finger loop trigger 104 each include a finger loop, whereby the main body 102 and the finger loop trigger 104 are operated by a hand of a user in a scissor-type fashion.

The generally cylindrical housing 118 is coupled to the main body 102 at a first end of the housing 118 and extends outward from the main body 102. The upper biter jaw 108 is coupled to a second end of the housing 118 distal to the main body 102. In the present embodiment, the upper biter jaw 108 is fixedly coupled to the probe housing 118, i.e. is stationary. The lower biter jaw 110 is pivotally coupled to a link rod 204 at least partially housed within the housing 118. The combination of the upper biter jaw 108 and the lower biter jaw 110 forms a moveable jaw. The upper biter jaw 108 and the lower biter jaw 110 include an inner biting surfaces. The cutting surface may be teeth, razors, or other surface configured for cutting tissue gripped in the jaw. The lower biter jaw 110 is coupled to an end of the link rod 204 proximate to the second end of the housing 118. The link rod 204 is coupled to and operated by the finger loop trigger 104. The finger loop trigger 104 is pivotally coupled to the main body 102 at the pivot connection 114.

The probe 106 is housed within the housing 118 and operatively coupled to the dial 112 and the retraction trigger 116. A portion of the probe 106 extends past the second end of the housing 118. The probe 106 is generally cylindrical and a portion of the probe end extending past the housing 118 is bent at approximately 90 degrees in a hook. In some embodiments the probe 106 is rotatable. The probe 106 comprises an elastic material that can elastically bend sharply with the ability to return to an original linear configuration when retracted back into the housing 118, such as a shape-memory alloy. Examples of suitable elastic material include, but are not limited to, nitonal or spring steel. In some embodiments, an exposed (visible) portion of the probe 106 include a plurality of measurement markings. The measurement markings may be used, for example, to measure the damage to the meniscus.

In some embodiments in lieu of the hooked end of the probe 106, the end of the probe 106 may comprise an additional jaw, whereby the instrument 100 includes an extendable jaw and a nonextendable jaw. The extendable jaw may encompass the upper and lower biter jaws 108, 110, or the upper and lower biter jaws 108, 110 may encompass the extendable jaw. In other embodiments, the extendable jaw and the upper and lower biter jaws 108, 110 are located side-by-side.

Figure 2:
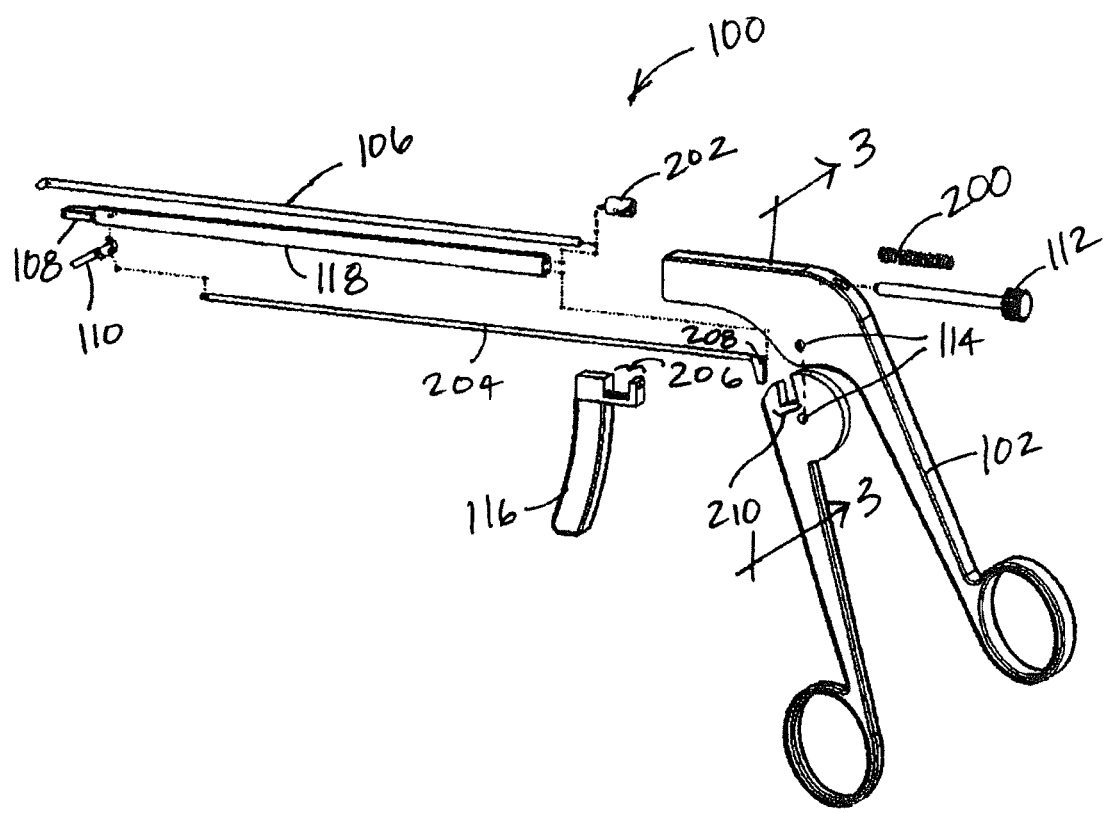
FIG. 2 is a side elevational exploded view of the meniscal biter instrument.

Referring next to FIG. 2, a side elevational exploded view of the meniscal biter instrument 100 is shown. Shown are the main body 102, the finger loop trigger 104, the probe 106, the upper biter jaw 108, the lower biter jaw 110, the dial 112, the pivot connection 114, the retraction trigger 116, the housing 118, a spring 200, a drum 202, a link rod 204, a trigger notch 206, a tooth 208, and a loop trigger notch 210.

The main body 102 houses the entire mechanism. The finger loop trigger 104 is pivotally coupled to the main body 102 at the pivot connection 114. The finger loop trigger 104 includes the loop notch encased in the main body 102 and configured to receive the tooth 208 at and a first end of the link rod 204 proximate to the main body 102.

The housing 118 is coupled to the main body 102 at a first housing end and extends outward from the main body 102. The upper biter jaw 108 is coupled to a second housing end distal to the main body 102. The probe 106 is housed within a bore in the housing 118 and extends through the upper biter jaw 108 via a bore aligned with the housing bore. A first end of the probe 106 proximate to the main body 102 is coupled to the drum 202. The drum 202 is located within the trigger notch 206 and is coupled to and operated by the dial 112. The spring 200 is disposed to automatically keep the retraction trigger 116 in a forward state, whereby when there is no action on the retraction trigger 116, the probe 106 is automatically kept in a forward (extended) position. The spring 200 is compressed when the retraction trigger 116 is moved rearwards.

The link rod 204 may be housed within an additional bore in the housing 118 as shown in FIG. 2 or may run within a channel in the housing 118. A second end of the link rod 204 distal to the main body 102 is pivotally coupled to the lower biter jaw 110.

Figure 3:
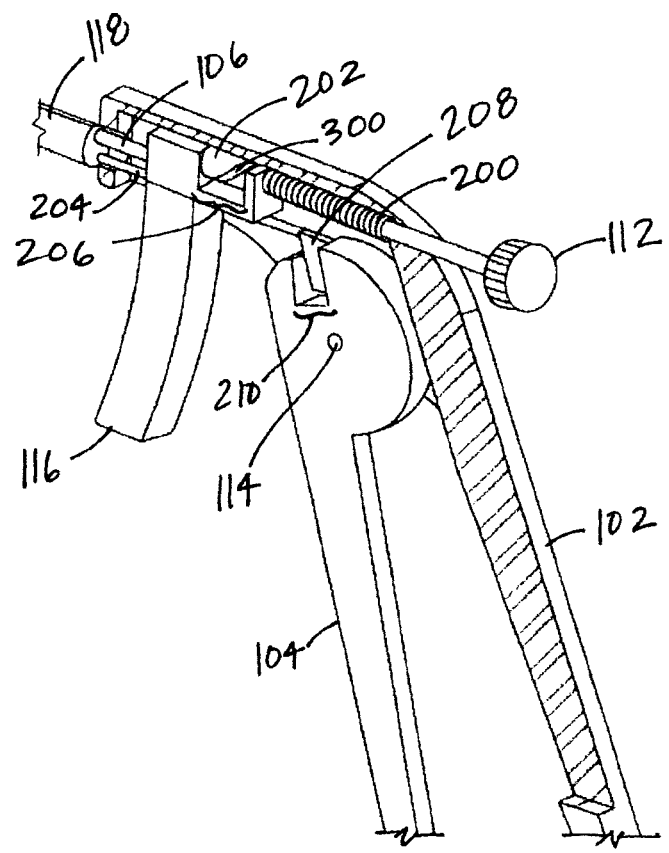
FIG. 3 is an interior perspective view of a portion of a main body of the meniscal biter instrument.

Referring next to FIG. 3, an interior perspective view of a portion of the main body 102 of the meniscal biter instrument 100 showing the operative mechanism is shown. Shown are the main body 102, the finger loop trigger 104, the probe 106, the dial 112, the pivot connection 114, the retraction trigger 116, the housing 118, the spring 200, the drum 202, the link rod 204, the trigger notch 206, the tooth 208, the loop trigger notch 210, and the spiral groove 300.

The lower biter jaw 110 (coupled to the link rod 204) is operated using the single tooth gear mechanism of the tooth 208 seated in the loop trigger notch 210. When the finger loop trigger 104 is pivoted around the pivot connection 114, the lower biter jaw 110 is actuated.

The probe 106 is operated by the dial 112 located on the back end of the main body 102. Turning of the dial 112 rotates the drum 202. The drum 202 includes the single spiral groove 300. The first end of the probe 106 is inserted in the spiral groove 300, whereby the probe 106 moves either outward from the housing 118 or inward, depending on the direction of rotation of the dial 112.

The probe 106 is also coupled to and operated by the retraction trigger 116. The spring 200 is in compression and automatically keeps the probe 106 and retraction trigger 116 in the forward (extended, probing) position in its normal state. The housing 118 controls the position of the probe 106 relative to the front and rear of the instrument 100. The probe 106 is connected to the main body 102 of the device 100 that is directly attached to the retraction trigger 116. By pulling the retraction trigger 116 rearwards, the probe 106 is also pulled rearwards which retracts the probe 106 to a position closer to the lower biter jaw 110 and upper biter jaw 108. The retraction trigger 116 that retracts the probe 106 functions independently from the dial 112 that controls the extrusion of the probe 106.

Generally, the meniscal biter instrument comprises the main body 102 configured to be held by one hand. The cutting mechanism, shown in FIGS. 1-3 as the biter jaws 108, 110 and their actuating mechanism, is coupled to the main body 102 and configured to be operated by the same hand while being held. In the embodiment shown, the cutting mechanism is operated using the finger loop trigger 104. The extendable probe 106 is also coupled to the main body 102 and is operable by the same hand while being held. In the embodiment shown, the extendable probe 106 is automatically extended with the spring 200 mechanism in the main body 102 and retracted by the hand using the retraction trigger 116 coupled to the main body 102.

Referring again to FIGS. 1-3, the combination meniscal biter instrument 100 is shown in one embodiment of the present invention. Conventional meniscal surgery uses a biter instrument and a separate probe instrument operated by different hands. The combination meniscal biter instrument 100 disclosed herein allows the biter instrument and probe 106 to be operated single-handedly.

In some embodiments all or portions of the meniscal biter instrument 100 and/or removable probe instrument are reusable. In other embodiments all or portions of the meniscal biter instrument 100 and/or removable probe instrument are disposable.

Figure 4:
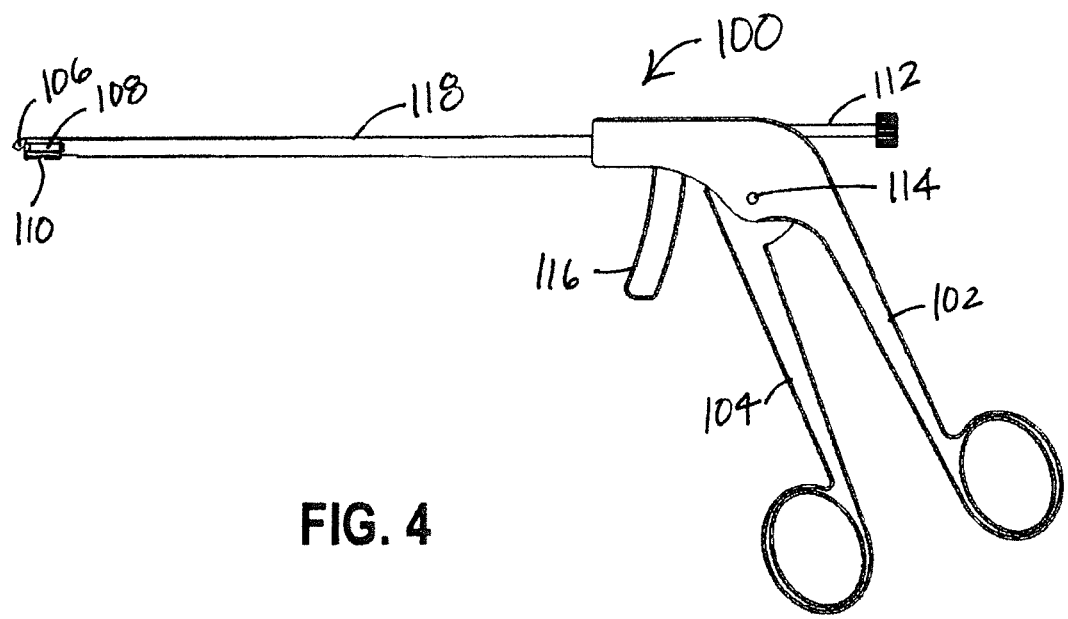
FIG. 4 is a side elevational view of the meniscal biter instrument in a fully retracted state.

Referring next to FIG. 4, a side elevational view of the meniscal biter instrument 100 in a fully retracted state is shown. Shown are the main body 102, the finger loop trigger 104, the probe 106, the upper biter jaw 108, the lower biter jaw 110, the dial 112, the pivot connection 114, the retraction trigger 116, and the housing 118.

FIG. 4 shows the instrument 100 in a fully concealed state prior to insertion into a knee capsule. The probe 106 is fully retracted within the housing 118. To fully retract the probe 106 and maintain the probe 106 in the retracted position, the surgeon must pull and hold the retraction trigger 116 at the rearmost position shown in FIG. 4. The finger loop trigger 104 is rotated to the rearmost position, whereby the lower biter jaw 110 is in the upward position, i.e. in a closed position with respect to the upper biter jaw 108.

Figure 5:
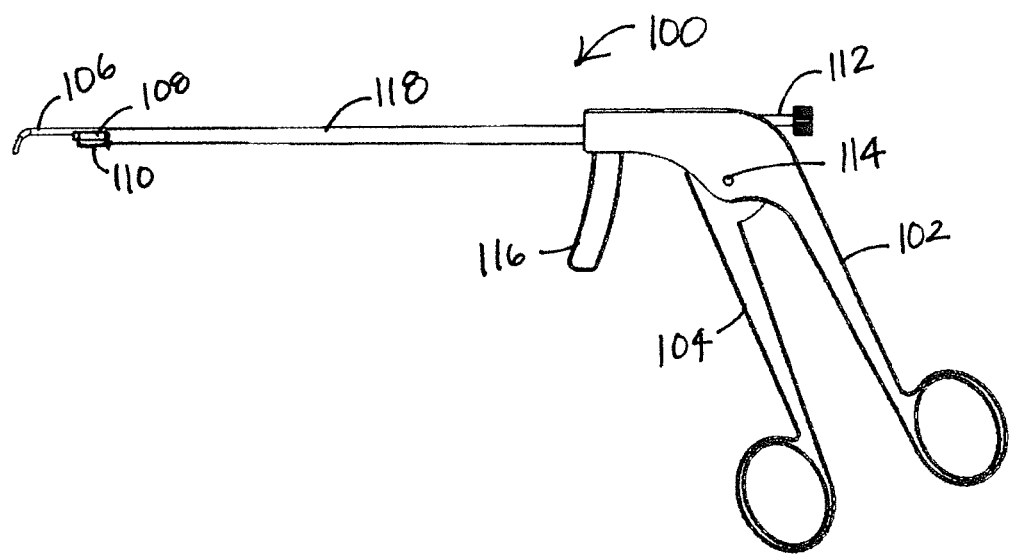
FIG. 5 is a side elevational view of the meniscal biter instrument in a state with a probe extended.

Referring next to FIG. 5, a side elevational view of the meniscal biter instrument 100 in a state with the probe 106 extended. Shown are the main body 102, the finger loop trigger 104, the probe 106, the upper biter jaw 108, the lower biter jaw 110, the dial 112, the pivot connection 114, the retraction trigger 116, and the housing 118.

FIG. 5 shows the instrument 100 in a state with the probe 106 extended but prior to resection of the meniscal tissue (i.e. the lower biter jaw 110 is still in the closed position). The probe 106 is extruded from the housing 118 by turning the dial 112. The probe 106 at its furthest displacement from the main body 102 is configured to allow surveying and probing of the meniscal tissue.

Figure 6:
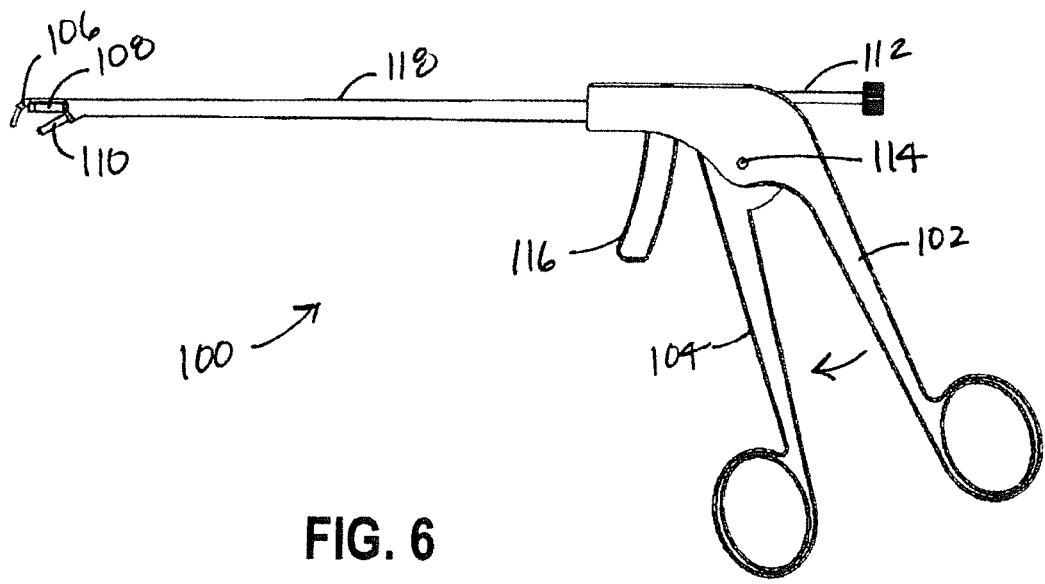
FIG. 6 is a side elevational view of the meniscal biter instrument in a state with the probe extended and a lower jaw articulated.

Referring next to FIG. 6, a side elevational view of the meniscal biter instrument 100 in a state with the probe 106 extended and the lower biter jaw 110 articulated is shown. Shown are the main body 102, the finger loop trigger 104, the probe 106, the upper biter jaw 108, the lower biter jaw 110, the dial 112, the pivot connection 114, the retraction trigger 116, and the housing 118.

FIG. 6 shows the instrument 100 in an open state prior to resection of the meniscal tissue. The probe 106 is retracted via the retraction trigger 116 as previously described. The finger loop trigger 104 is rotated forward, operating the tooth mechanism and actuating the lower biter jaw 110 downward to the open position. The finger loop trigger 104 is then rotated rearward, closing the lower biter jaw 110 to remove the damaged meniscal tissue. The probe 106 will be on the other end of the meniscus that is under operation to ensure that the meniscus does not slip out and away from the biter jaws 108, 110 during the biting action (cutting).

In some embodiment, an extendable probe assembly may be coupled to an existing biter instrument in order to modify conventional biter instruments as known in the art. In lieu of incorporating the probe 106 within the biter mechanism housing 118 as previously shown, the probe 106 may be coupled to a housing of a stand-alone conventional biter instrument. The probe assembly would include a retraction handle located proximate to the held portion of the biter instrument, whereby the probe 106 may be operated by the hand holding the biter instrument. One embodiment of removable extendable probe is shown below in FIGS. 25-28.

Figure 7:
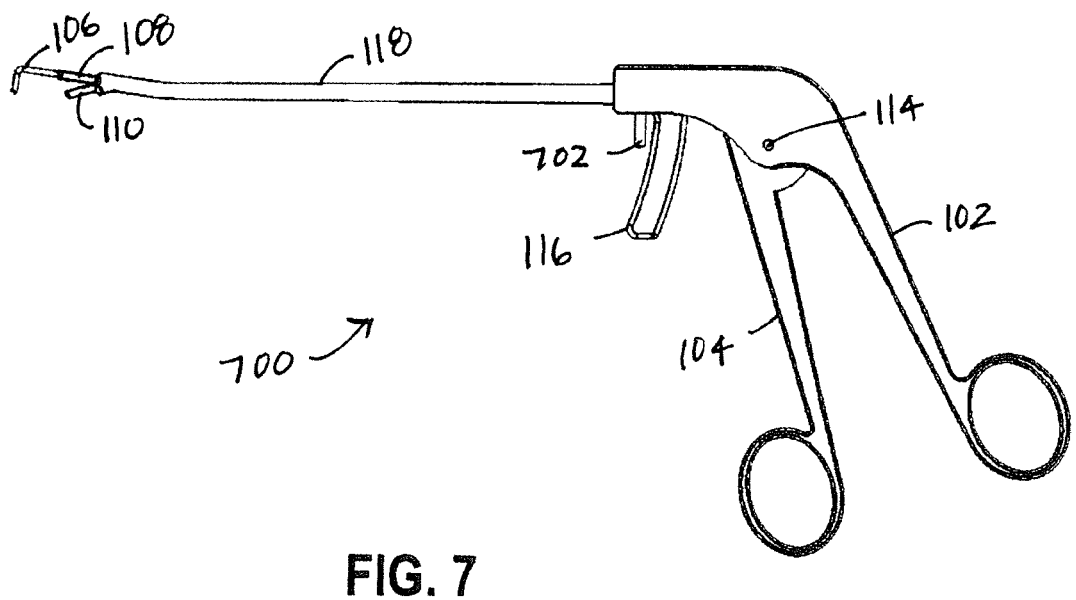
FIG. 7 is a side elevational view of a meniscal biter instrument in another embodiment of the present invention.

Referring next to FIG. 7, a side elevational view of a meniscal biter instrument 700 in another embodiment of the present invention is shown. Shown are the main body 102, the finger loop trigger 104, the probe 106, the upper biter jaw 108, the lower biter jaw 110, the pivot connection 114, the retraction trigger 116, the housing 118, and the probe rotation trigger 702.

In the embodiment of FIG. 7, the end of the housing 118 distal to the main body 102 is angled upwards. In one embodiment, the angle is between 0 and 15 degrees. The angle allows the surgeon to better access the posterior menisci of the knee. The embodiment of FIG. 7 also includes the probe rotation trigger 702 coupled to the retraction trigger 116.

Figure 8:
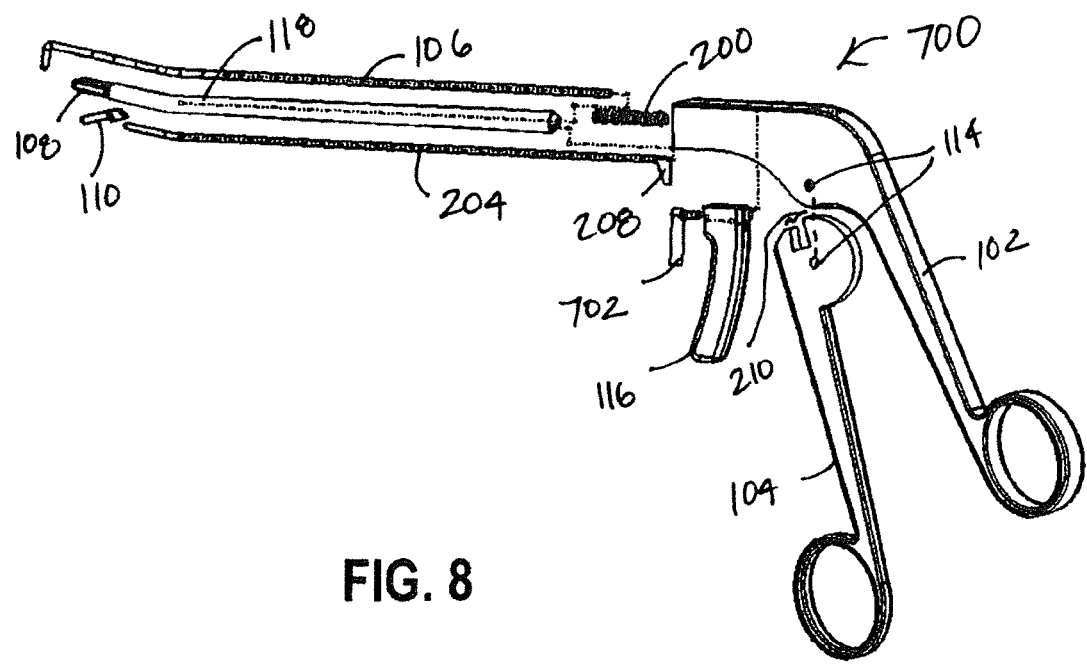
FIG. 8 is a side elevational exploded view of the meniscal biter instrument of FIG. 7.

Referring next to FIG. 8, a side elevational exploded view of the meniscal biter instrument 700 of FIG. 7 is shown. Shown are the main body 102, the finger loop trigger 104, the probe 106, the upper biter jaw 108, the lower biter jaw 110, the pivot connection 114, the retraction trigger 116, the housing 118, the spring 200, the link rod 204, the and the probe rotation trigger 702.

The meniscal biter instrument 700 of FIGS. 7 and 8 does not include the dial 112 of the previous embodiment. The spring 200 is disposed within the main body 102 such that in the normal position the spring 200 is interposed between the retraction trigger 116 and a rear wall of the main body 102, whereby the spring 200 automatically pushes the probe 106 outward in the fully extended position. As before, the probe 106 is retracted by pulling the retraction trigger 116 rearward.

The housing 118 includes a channel 900 cutout on the underside of the housing 118 to accommodate the link rod 204, in addition a bore 902 configured to house the probe 106. The probe rotation trigger 702 is mounted on the front face of the retraction trigger 116. The probe rotation trigger 702 is coupled to the probe 106 inside the main body 102. Rotation of the probe rotation trigger 702 causes the probe 106 to also rotate within the bore 902. In use, when the instrument 700 is being inserted into the knee the surgeon rotates the probe rotation trigger 702 such that the bent end of the probe 106 is on a parallel plane with the upper biter jaw 108, as shown below in FIG. 10. Once inside the knee, the probe 106 is extruded forward as previously described and rotated 90 degrees downward using the probe rotation trigger 702, as shown below in FIG. 11. The probe rotation trigger 702 is mounted on the front face of the retraction trigger 116, allowing the probe 106 to translate back and forth while in the downward position.

Figure 9:
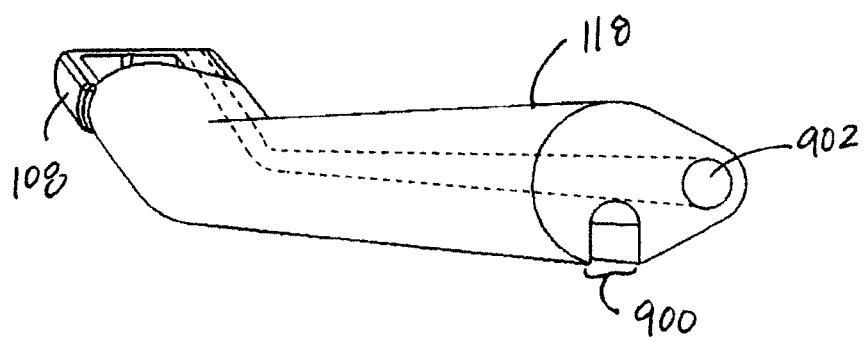
FIG. 9 is a perspective view of a probe casing of the meniscal biter instrument.

Referring next to FIG. 9, a rear perspective view of the housing 118 of the meniscal biter instrument 700 of FIGS. 7 and 8 is shown. Shown are the upper biter jaw 108, the channel 900, and the bore 902.

The housing 118 in the embodiment of FIGS. 7 and 8 includes the channel 900 included in the underside of the housing 118 configured to house the link rod 204. The bore 902 extends the length of the housing 118 and is configured to house the probe 106.

Figure 10:
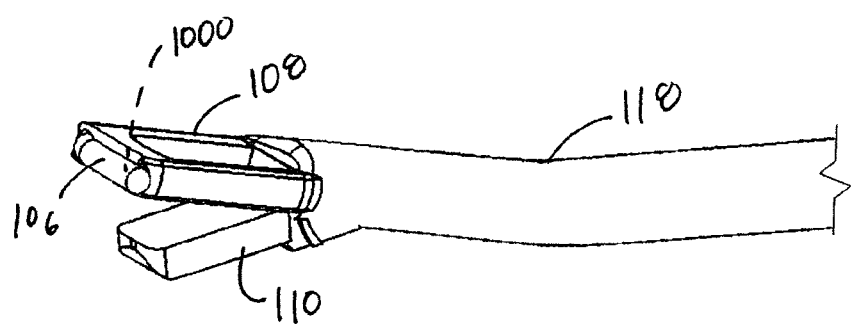
FIG. 10 is a perspective view of a biter end of the meniscal biter instrument with the probe retracted.

Referring next to FIG. 10, a perspective view of the distal (biter) end of the meniscal biter instrument 700 with the probe 106 retracted is shown. Shown are the housing 118, the upper biter jaw 108, the lower biter jaw 110, the probe 106, and a depression 1000.

As shown in FIG. 10, the upper biter jaw 108 is an approximate U-shape, with the legs of the U-shape coupled to the housing 118. The outward face of the upper biter jaw 108 includes the depression 1000 running along the length of the base of the U-shape and is configured to seat the bent end of the probe 106 when the probe 106 is retracted and the bent end of the probe 106 aligned with the depression 1000. In the embodiment shown, the probe 106 extends through one of the v legs and is above the hinge point of the lower biter jaw 110. The lower biter jaw 110 as shown is a solid rectangular shape.

Figure 11:
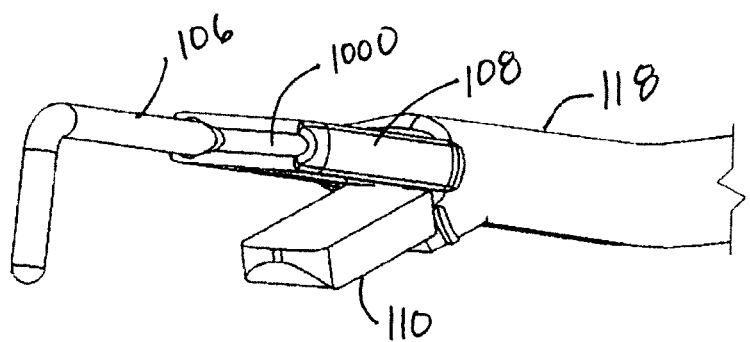
FIG. 11 is a perspective view of the biter end of the meniscal biter instrument with the probe extended.

Referring next to FIG. 11, a perspective view of the biter end of the meniscal biter instrument 700 with the probe 106 extended is shown. Shown are the housing 118, the upper biter jaw 108, the lower biter jaw 110, the probe 106, and the depression 1000.

In FIG. 11 the probe 106 is shown extended and with the bent end of the probe 106 rotated downward as previously described. The channel 900 running the length of the upper biter jaw 108 is visible in FIG. 11.

Figure 12:
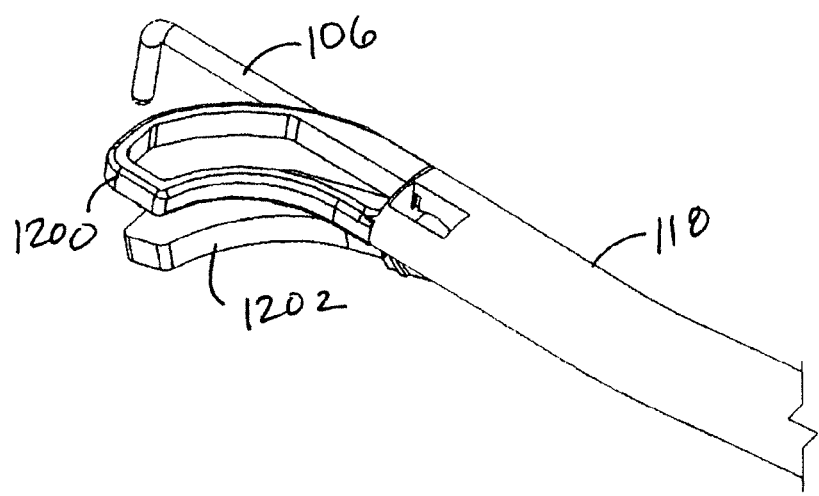
FIG. 12 is a perspective view of an angled biter end of the meniscal biter instrument in accordance with another embodiment of the present invention.

Referring next to FIG. 12, a perspective view of an angled jaw of a meniscal biter instrument in accordance with another embodiment of the present invention is shown. Shown are the housing 118, the probe 106, the angled upper biter jaw 1200 and the angled lower biter jaw 1202.

The angled upper biter jaw 1200 also includes two legs and a connecting portion, but the connecting portion is curved sideways away from the probe location, forming an overall arcuate upper biter jaw shape. The angled lower biter jaw 1202 is shaped similarly to the angled upper biter jaw 1200, but is a solid shape.

In general, in the alternate embodiment shown in FIG. 12, the angled upper biter jaw 1200 and the angled lower biter jaw 1202 are curved, rounded, and otherwise configured to be more conforming to the shape of the menisci.

Figure 13:
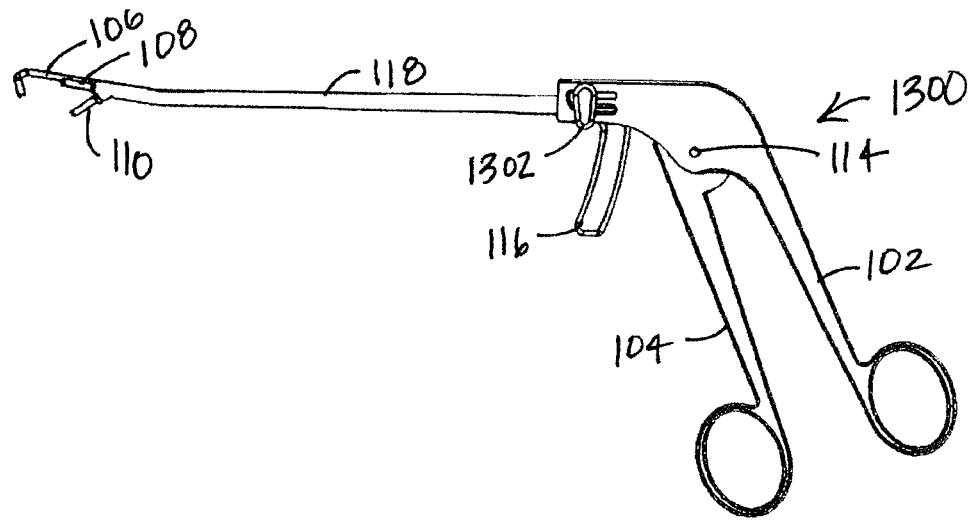
FIG. 13 is a side elevational view of a meniscal biter instrument in yet another embodiment of the present invention.

Referring next to FIG. 13, a side elevational view of a meniscal biter instrument 1300 in yet another embodiment of the present invention is shown. Shown are the main body 102, the finger loop trigger 104, the probe 106, the upper biter jaw 108, the lower biter jaw 110, the pivot connection 114, the retraction trigger 116, the housing 118, and a knob 1302.

The embodiment shown in FIG. 13 includes the knob 1302 coupled to the retraction trigger 116 and configured to control a cable 1400 running inside the hollow probe 106.

Figure 14:
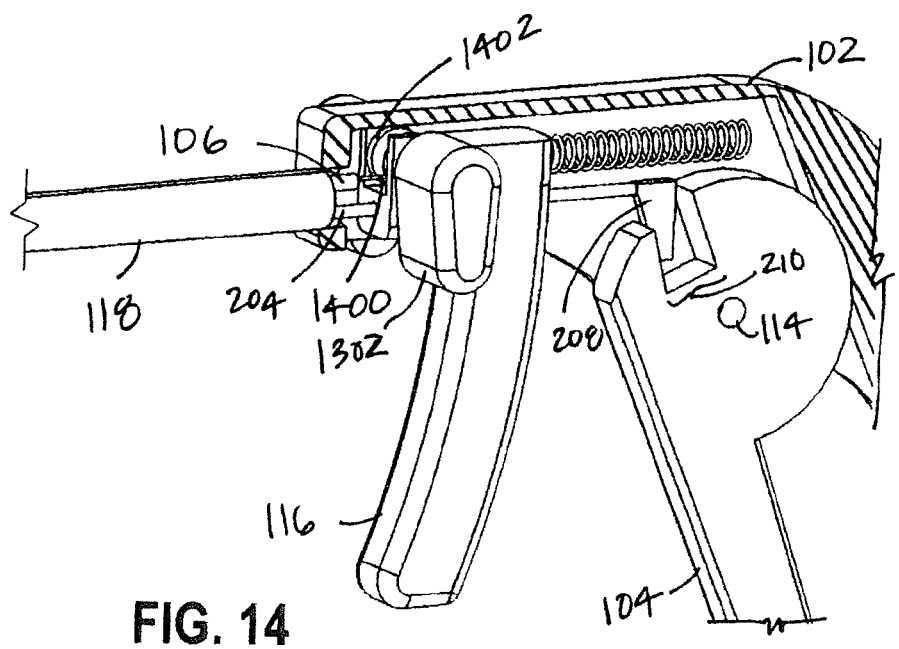
FIG. 14 is an interior perspective view of a portion of a main body of the meniscal biter instrument of FIG. 13.

Referring next to FIG. 14, an interior perspective view of a portion of the main body 102 of the meniscal biter instrument 1300 of FIG. 13 showing the operative mechanism is shown. Shown are the main body 102, the finger loop trigger 104, the probe 106, the pivot connection 114, the retraction trigger 116, the housing 118, the spring 200, the link rod 204, the tooth 208, the loop trigger notch 210, the knob 1302, the cable 1400, and a spool 1402.

In the embodiment of FIGS. 13 and 14, probe 106 is hollow and includes the cable 1400 anchored at the end of the probe 106 distal to the main body 102 and running through the probe 106 to the interior of the main body 102. The probe 106 in the present embodiment also comprises multiple sectional pieces. After the cable 1400 exits the probe 106, the cable 1400 is coupled to the spool 1402 rotationally housed in the retraction trigger 116. The spool 1402 is operatively coupled to the exterior knob 1302 such that rotation of the knob 1302 rotates the spool 1402, whereby the cable 1400 is either wrapped around the spool 1402 or loosened from the spool 1402, depending on the direction of rotation of the spool 1402. In one embodiment, the knob 1302 is configured to rotate 90 degrees from an initial positon.

In operation, in the initial position of the knob 1302, the cable 1400 is loosened and open spaces exist between the multiple sectional pieces of the probe 106. When the knob 1302 is rotated 90 degrees, the cable 1400 is tightened onto the spool 1402, bringing the sectional pieces of the probe 106 together and creating a curved tip of the probe 106. The probe 106 remains curved as long as the knob 1302 remains in the rotated position. Because the elements used for creating the curved tip are all mounted on the retraction trigger 116, the curved probe 106 may translate back and forth by moving of the retraction trigger 116, as previously described.

Figure 15:
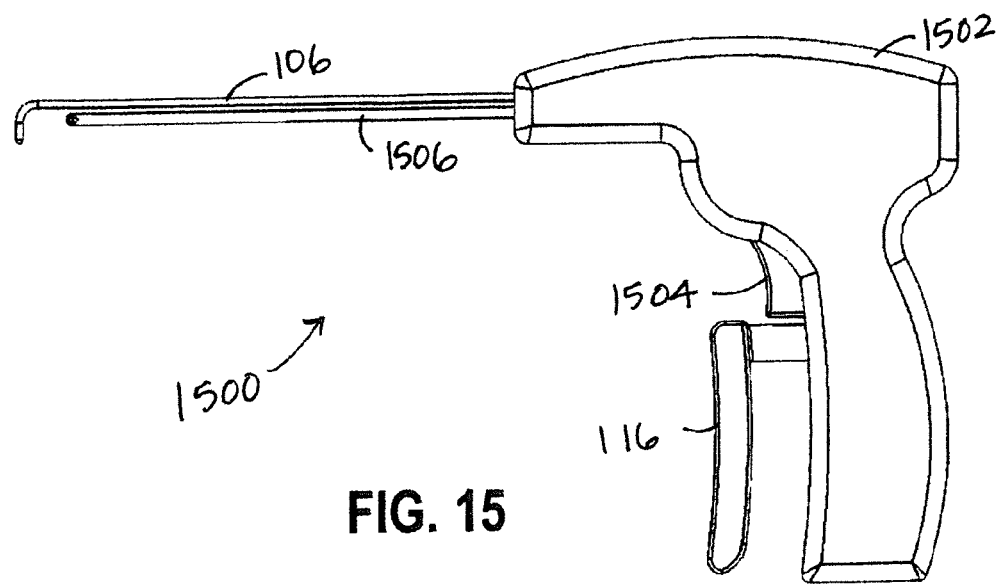
FIG. 15 is a side elevational view of an electric meniscal sculptor in one embodiment of the present invention.

Referring next to FIG. 15, a side elevational view of an electric meniscal sculptor 1500 in yet another embodiment of the present invention is shown. Shown are the probe 106, the retraction trigger 116, a sculptor housing 1502, a shaver trigger 1504, and a shaver housing 1506.

The sculptor housing 1502 is in a general handgun shape, with the probe 106 and the shaver housing 1506 extending from the "barrel" portion of the sculptor housing 1502 and the "grip" portion of the sculptor housing 1502 configured for holding by the surgeon. The grip portion includes the retraction trigger 116 located on the front side of the grip and operable by a hand holding the grip. The grip also includes the shaver trigger 1504, also mounted to the front side of the grip and operable by the hand holding the grip.

Figure 16:
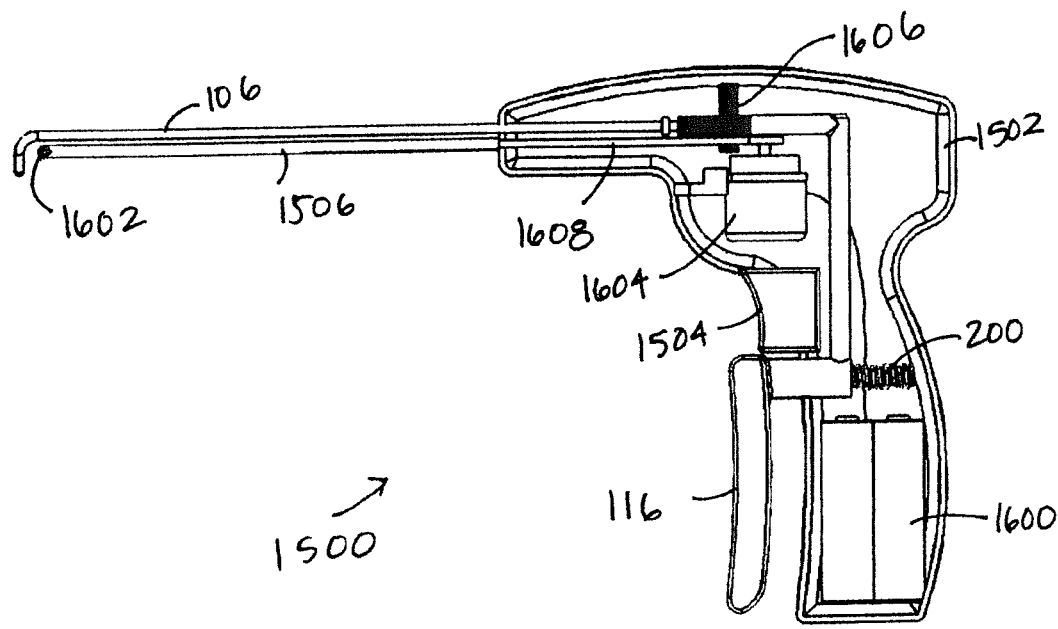
FIG. 16 is a side interior view of the electric meniscal sculptor.

Referring next to FIG. 16, a side interior view of the electric meniscal sculptor 1500 showing the operative mechanism is shown. Shown are the probe 106, the retraction trigger 116, the spring 200, the sculptor housing 1502, the shaver trigger 1504, and the shaver housing 1506, a power source 1600, a shaver blade 1602, a motor 1604, a rotation wheel 1606, and a shaver rod 1608.

Similar to previous embodiments, the spring 200 is coupled to the retraction trigger 116 coupled to the probe 106, whereby the spring 200 keeps the probe 106 in the extended position unless the retraction trigger 116 is moved closer to the sculptor housing 1502. The rotation wheel 1606 is coupled to the probe 106 and is configured to rotate the probe 106 to a maximum rotation angle of about 90 degrees, such that the bent end of the probe 106 can rotated between a generally horizontal position and a downward position in order to keep the total height of the parts that are in the knee at a minimum during the entering and exiting of the portal of the knee. A portion of the rotation wheel 1606 extends beyond the housing 1502 to allow for manipulation by the surgeon. The rotation wheel 1606 may be a knob, button or trigger, and may be manually or electrically controlled by the surgeon.

The shaver blade 1602 is coupled to a shaver end of the shaver rod 1608 distal to the sculptor housing 1502. The shaver rod 1608 is housed within the tubular shaver housing 1506, which in turn is coupled to the motor 1604, whereby the shaver blade 1602 is driven by the motor 1604. The motor 1604 is electrically coupled to and powered by the power source 1600 located within the sculptor housing 1502. In the embodiment shown, the power source 1600 comprises at least one battery.

Figure 17:
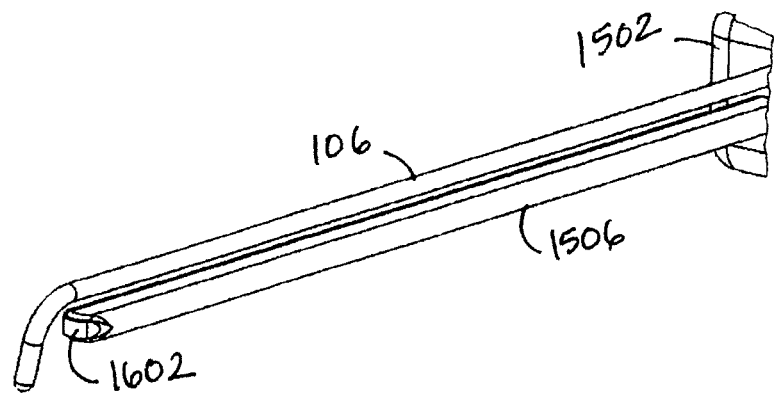
FIG. 17 is a perspective view of a shaver end of the electric meniscal sculptor.

Referring next to FIG. 17 a perspective view of the shaver end of the electric meniscal sculptor 1500 is shown. Shown are the sculptor housing 1502, the probe 106, the shaver housing 1506, and the shaver blade 1602.

As previously described, the shaver blade 1602 extends from the forward edge of the shaver housing 1506 and faces forward, i.e. the shaver blade 1602 is mounted directly on the front of the shaver housing 1506. The shaver blade 1602 is oriented generally horizontally and has an elliptical profile. In the configuration shown, the probe 106 is located above the shaver housing 1506, but other suitable configurations may also be used.

Figure 18:
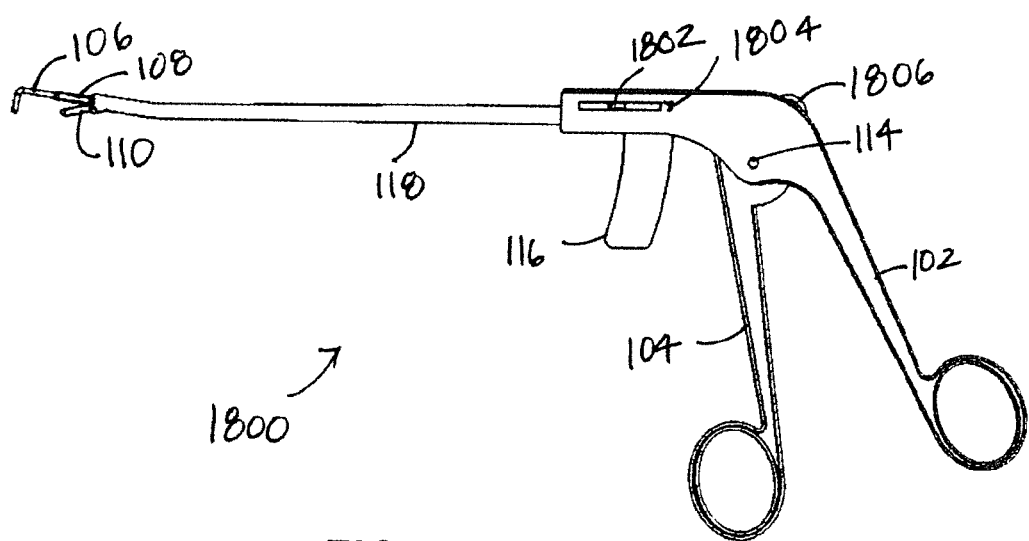
FIG. 18 is a side elevational view of a meniscal biter instrument in another embodiment of the present invention.

Referring next to FIG. 18, a side elevational view of a meniscal biter instrument 1800 in yet another embodiment of the present invention. Shown are the main body 102, the finger loop trigger 104, the probe 106, the upper biter jaw 108, the lower biter jaw 110, the pivot connection 114, the retraction trigger 116, the housing 118, an arm 1802, a slot 1804, and a spring pin 1806.

The meniscal biter instrument 1800 of FIG. 18 is similar to the meniscal biter instrument 700 of FIG. 7, with the exclusion of the probe rotation trigger 702 and inclusion of the arm 1802 and the slot 1804. The slot 1804 is located on the main body 102 and allows the arm 1802 to protrude from the interior of the main body 102 and slide within the generally horizontal slot 1804.

Figure 19:
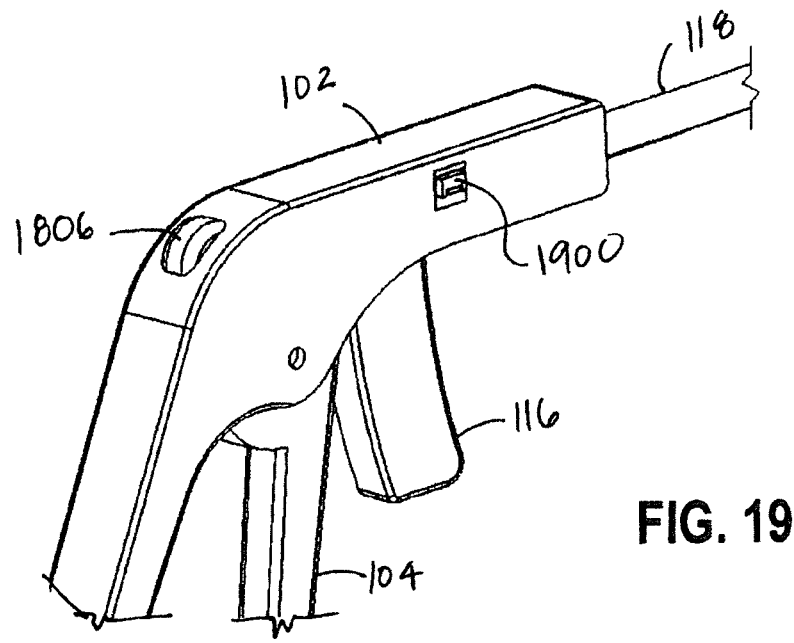
FIG. 19 is a rear perspective view of a portion of a main body of the meniscal biter instrument of FIG. 18 with a probe rotation button in a first position.

Referring next to FIG. 19, an opposite side perspective view of a portion of the main body 102 of the meniscal biter instrument 1800 of FIG. 18 is shown with a probe rotation button 1900 in a first position is shown. Shown are the main body 102, the finger loop trigger 104, the housing 118, the spring pin 1806, and the probe rotation button 1900.

The meniscal biter instrument 1800 includes the probe rotation button 1900 coupled to a rack-and-pinion mechanism housed within the main body 102. The rack-and-pinion mechanism is coupled to and is configured to rotate the probe 106. The probe rotation button 1900 is accessible to the surgeon view an opening in the main body 102 slightly larger than the probe rotation button 1900. In the first position, the button 1900 extends past the main body 102 through the hole. When the probe rotation button 1900 is in the first position, the probe 106 is held in the retracted and unrotated state, such as shown in FIG. 10.

Figure 20:
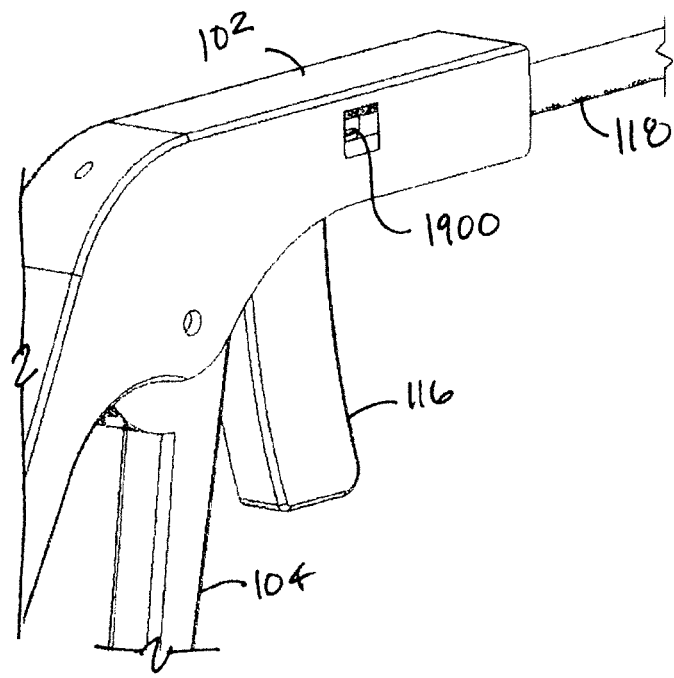
FIG. 20 is a rear perspective view of a portion of a main body of the meniscal biter instrument of FIG. 18 with a probe rotation button in a second position.

Referring next to FIG. 20, the opposite side perspective view of the portion of the main body 102 of the meniscal biter instrument 1800 of FIG. 18 is shown with the probe rotation button 1900 in a second position. Shown are the main body 102, the finger loop trigger 104, the housing 118, and the probe rotation button 1900.

The meniscal biter instrument 1800 is shown after the surgeon has horizontally pushed in the probe rotation button 1900. Pushing in the probe rotation button 1900 moves the rack-and-pinion mechanism and the probe 106 horizontally, causing the probe 106 to align with the interior spring 200, which then acts on the probe 106 to extend the probe 106. The probe rotation button 1900 is also moved forward within the main body 102, causing the button 1900 to be unaligned with the hole and keeping the probe 106 aligned with the spring 200 and in the extended position. Pushing the probe rotation button 1900 also moves the rack of the rack-and-pinion mechanism, rotating a pinion 2100, which in turn rotates the probe 106 90 degrees downward from the original position to the rotated position.

Figure 21:
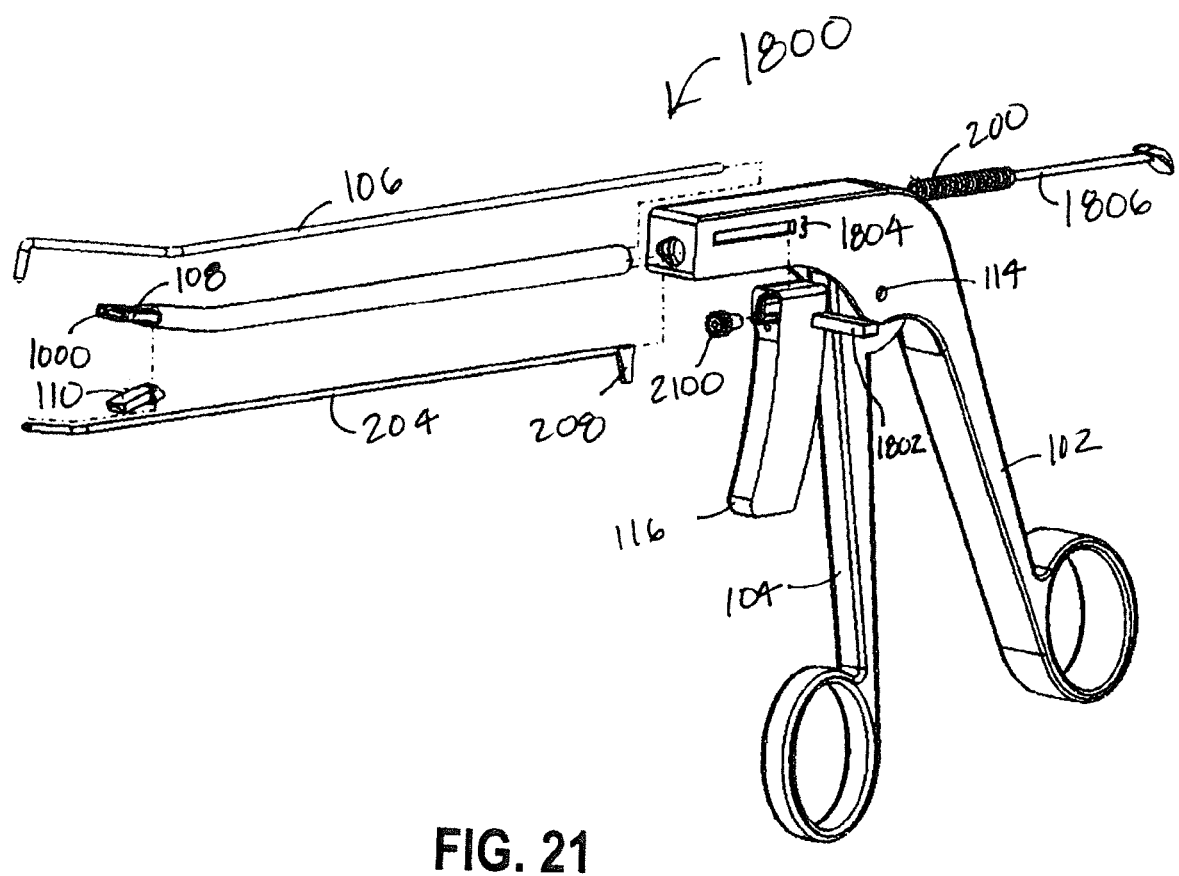
FIG. 21 is a perspective exploded view of the meniscal biter instrument of FIG. 18.

Referring next to FIG. 21, a perspective exploded view of the meniscal biter instrument 1800 of FIG. 18 is shown. Shown are the main body 102, the finger loop trigger 104, the probe 106, the upper biter jaw 108, the lower biter jaw 110, the pivot connection 114, the retraction trigger 116, the housing 118, the spring 200, the link rod 204, the tooth 208, the arm 1802, the slot 1804, the spring pin 1806, and the pinion 2100.

The retraction trigger 116 includes the arm 1802 coupled to the retraction trigger 116 and extending generally horizontally outward to the side through the generally horizontal slot 1804 in the main body 102. As the retraction trigger 116 is coupled to the probe 106, as the probe 106 is extended or retracted, the arm 1802 moves forward or rearward, respectively, along the slot 1804. The arm 1802 therefore provides a visual indicator on the main body 102 of the extension of the probe 106. When the end of the probe 106 is inside the patient's body and not visible to the surgeon, the surgeon can refer to position of the arm 1802 in the slot 1804 as a reference to the extension of the probe 106.

The pinion 2100 is coupled to the probe 106 such that rotation of the pinion 2100 rotates the probe 106. A corresponding rack, mounted internally in a portion of the retraction trigger 116, is coupled to the pinion 2100 for rotation of the pinion 2100 due to translation of the rack. The rack is coupled to the probe rotation button 1900, such that pushing in of the probe rotation button 1900 translates the rack, whereby the pinion 2100 is rotated, whereby the probe 106 is rotated.

Pushing in of the probe rotation button 1900 also shifts the probe 106 to the side, aligning the probe 106 with the spring 200. The spring 200 is kept in the location within the main body 102 by the spring pin 1806 running through the center of the spring 200.

Figure 22:
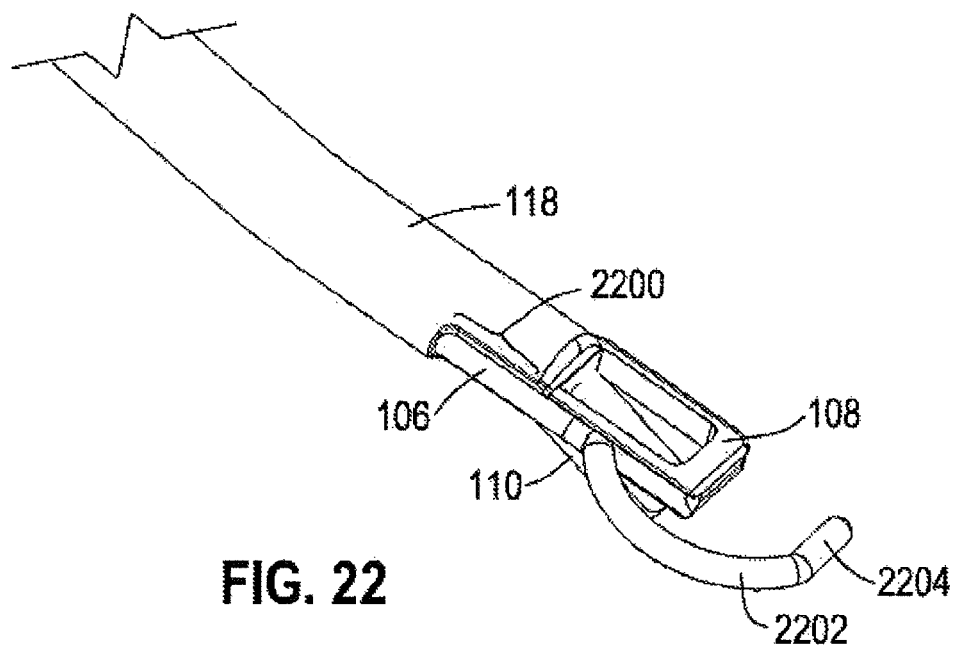
FIG. 22 is a perspective view of a probe end of the meniscal biter instrument in another embodiment of the present invention.

Referring next to FIG. 22, a perspective view of a probe end of an exemplary meniscal biter instrument in another embodiment of the present invention is shown. Shown are the probe 106, the upper biter jaw 108, the lower biter jaw 110, a housing cutaway 2200, an arcuate portion 2202, and a hook portion 2204

In another embodiment, the housing 118 includes the housing cutaway 2200 on a side of the housing 118. The cutaway 2200 extends to the second housing end at the probe location, whereby over the length of the cutaway 2200 an additional portion of the probe 106 is exposed before the second housing end. The cutaway 2200 provides additional freedom for the probe 106 to move relative to the second housing end and the biter jaws 108, 110. In one embodiment, the length of the housing cutaway 2200 is approximately 1 inch.

The probe 106 also includes the arcuate portion 2202 interposed between the lateral hook portion 2204 of the probe 106 and the generally linear probe portion continuing rearwards towards the main body 102. With the probe 106 in an unrotated position, the arcuate portion 2202 arcs away from the biter jaws 108, 100 in a generally horizontal plane. The arcuate portion 2202 comprises a generally shallow arc, with the arc ends generally aligning with the axis of the linear portion of the probe 106. The hook portion 2204 in the unrotated position extends generally horizontally towards the biter jaws 108, 110. The arcuate portion 2202 allows the probe 106 to have a greater lateral reach, whereby the probe 106 has better access to the meniscal tissue.

Figure 23:
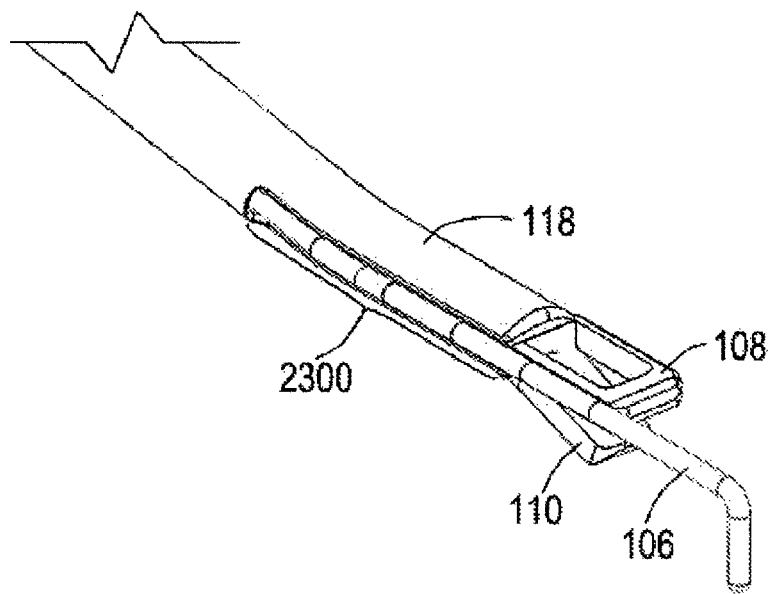
FIG. 23 is a perspective view of a probe end of the meniscal biter instrument in yet another embodiment of the present invention.

Referring next to FIG. 23, a perspective view of a probe end of an exemplary meniscal biter instrument in yet another embodiment of the present invention is shown. Shown are the probe 106, the upper biter jaw 108, the lower biter jaw 110, and an extended housing cutaway 2300.

In yet another probe embodiment, the housing 118 includes the extended housing cutaway 2300. The extended housing cutaway 2300 is similar to the housing cutaway 2200 of FIG. 22, with the exception that the extended cutaway portion extends further on the housing 118, whereby a greater length of probe 106 is exposed. The added exposure of the probe 106 relative to the location of the biter jaws 108, 110 provides even more freedom of movement of the probe 106 relative to the biter jaws 108, 110.

Figure 24:
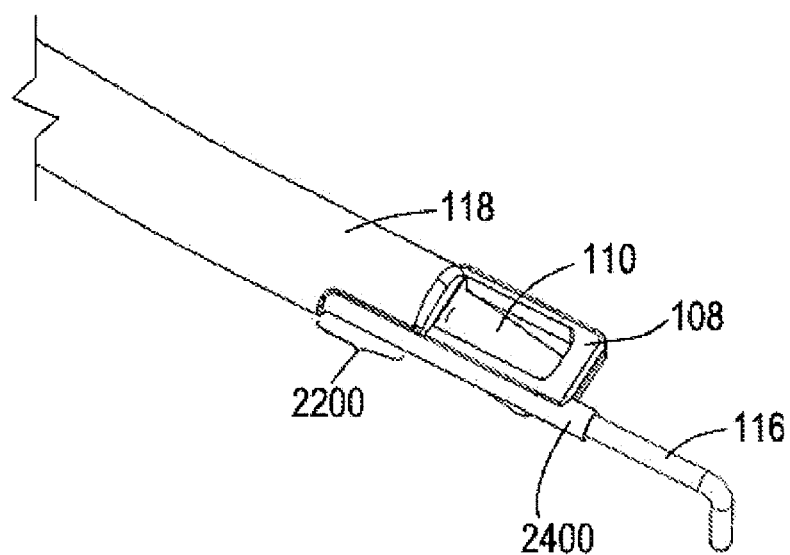
FIG. 24 is a perspective view of a probe end of the meniscal biter instrument in yet another embodiment of the present invention.

Referring next to FIG. 24, a perspective view of a probe end of the meniscal biter instrument in yet another embodiment of the present invention is shown. Shown are the probe 106, the upper biter jaw 108, the lower biter jaw 110, the housing cutaway 2200, and the telescoping portion 2400.

The probe embodiment of FIG. 24 includes the telescoping portion 2400 of the generally linear portion of the probe 106 exposed by the housing cutaway 2200. The telescoping portion 2400 extends with operation of the probe extension. The addition of the telescoping portion 2400 provides additional stiffness to the probe 106.

Figure 25:
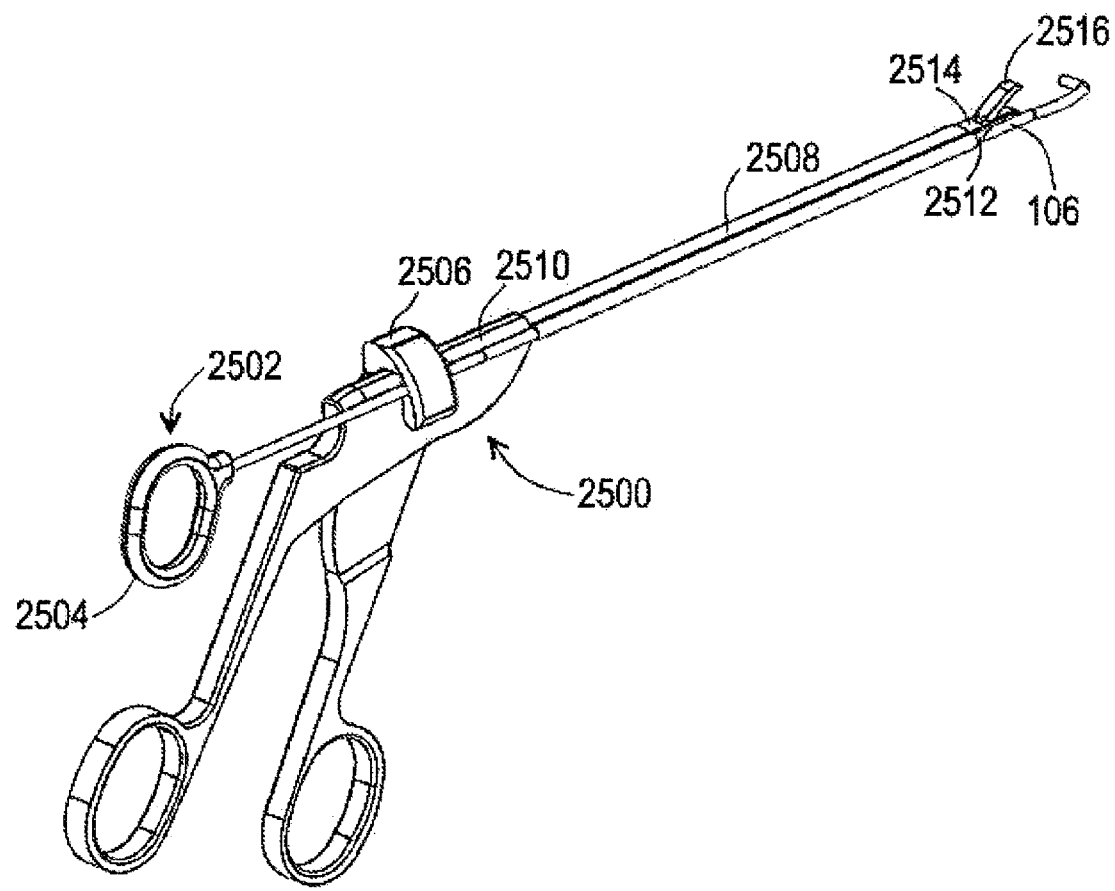
FIG. 25 is a perspective view of a probe assembly installed on a conventional biter device in another embodiment of the present invention.

Referring next to FIG. 25 a perspective view of a probe assembly 2502 installed on a biter device 2500 in another embodiment of the present invention is shown. Shown are the biter device 2500, the probe assembly 2502, the probe 106, a handle 2504, a mounting block 2506, a sleeve 2508, a biter device main body 2510, a metal sleeve 2512, a biter device shaft 2514, and a biter 2516.

The biter device 2500 is an example of an arthroscopic biting device (also known as a cutting device) as currently known in the art. It will be understood that the probe assembly 2502 may be configured to fit various embodiments of conventional biter devices in addition to the example biter device embodiment shown in FIG. 25.

The exemplary biter device 2500 includes the main body 2510 coupled to the biter device shaft 2514 extending away from the biter device main body 2510. The biter 2516 is coupled to an end of the shaft 2514 distal to the biter device main body 2510.

The probe assembly 2502 includes the handle 2504 coupled to an end of the probe 106 proximate to the biter device main body 2510. In some embodiments the handle 2504 is a finger loop. The probe 106 includes a length greater than a length of the shaft 2514 such that the probe 106 may be extended past the biter 2516. The mounting block 2506 is slidably coupled to the probe 106 a distance from the handle 2504 such that the probe 106 is operable when the mounting block 2506 is coupled to the biter device main body 2510 as shown in FIG. 25. In some embodiments the mounting block 2506 comprises plastic.

A portion of the probe 106 located between the mounting block 2506 and the end of the probe 106 distal to the handle 2504 slidably passes through a tubular portion of the sleeve 2508. The tubular portion may be a closed tube or may include a small longitudinal gap. The sleeve 2508 also includes the C-shaped channel parallel to the tubular portion of the sleeve 2508, which is coupled to the tubular portion such that the C-shaped portion opens generally downward and the tubular portion and the channel portion run side-by-side. The sleeve 2508 may be integrally formed. The extent and shape of the C-shaped channel are configured to removably snap to a portion of the shaft 2514, thus coupling the sleeve 2508 to the shaft 2514. It will be understood that other suitable methods of coupling the probe 106 to the biter instrument 2500 may be used.

In operation, the surgeon may extend and retract the probe 106 by pushing or pulling on the handle 2504, which slides the probe forwards or rearwards relative to the biter device 2500. In this embodiment, the addition of the probe assembly 2502 to the conventional biter instrument 2500 allows the surgeon to modify the conventional biter instrument 2500 for including the probe 106, and still providing for single-handed use of both the probe 106 and the biter device 2500.

Figure 26:
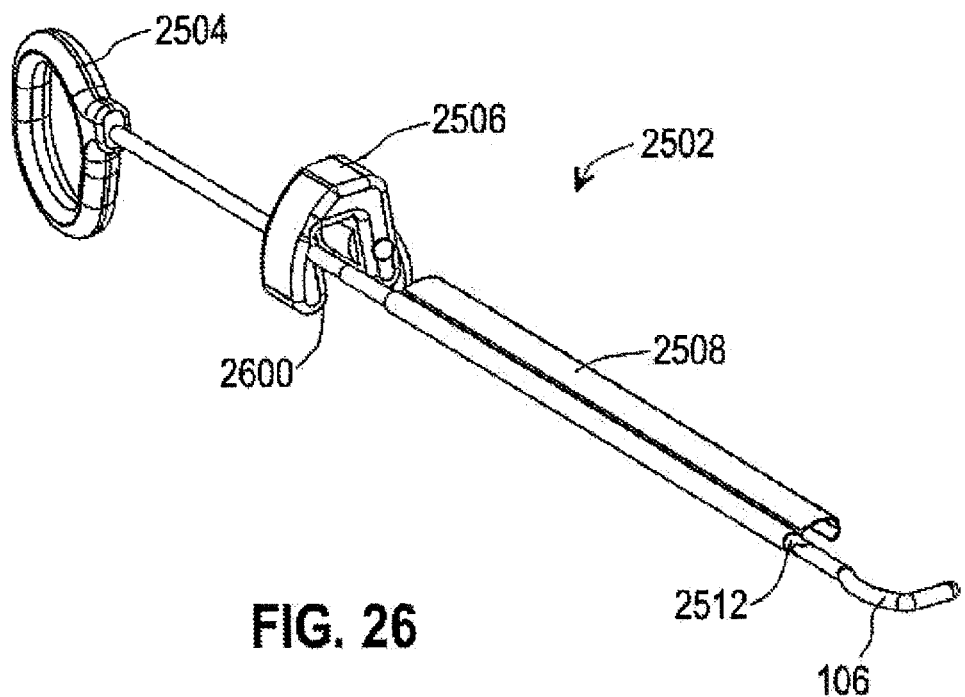
FIG. 26 is a front perspective view of the probe assembly.

Referring next to FIG. 26, a front perspective view of the probe assembly 2502 is shown. Shown are the probe assembly 2502, the probe 106, the handle 2504, the mounting block 2506, the sleeve 2508, the biter device main body 2510, the metal sleeve 2512, and a block notch 2600.

As previously described, the probe assembly 2502 includes the probe 106 extending away from the handle 2504. The probe is coupled to the mounting block 2506 at the distance from the handle 2504. The mounting block 2506 includes the block notch 2600 located at an underside of the mounting block 2506. The block notch 2600 is configured to fit over a top portion of the main body 2510 such that the probe 106 is located generally parallel to the shaft 2514. The mounting block 2506 includes a cam lever 2700 configured to clamp the probe assembly 2502 to the device main body 2510.

The probe assembly 2502 also include the sleeve 2508. As previously described, the probe 106 is slidable coupled to the sleeve 2508. The sleeve 2508 is clipped to the shaft 2514, further coupling the probe assembly 2502 to the device 2500 and providing additional restraint to the movement of the probe 106 relative to the biter 2516. The sleeve 2508 also includes the metal sleeve 2512 that fits inside the tubular portion of the sleeve 2508, with the probe passing through the metal sleeve 2512.

Figure 27:
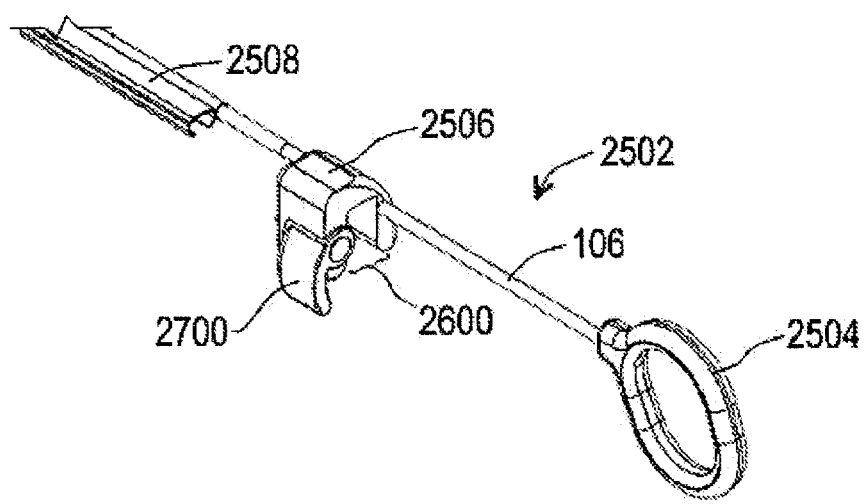
FIG. 27 is a partial rear perspective view of the probe assembly.

Referring next to FIG. 27, a partial rear perspective view of the probe assembly 2502 is shown. Shown are the probe assembly 2502, the probe 106, the handle 2504, the mounting block 2506, the sleeve 2508, the biter device main body 2510, the block notch 2600, and the cam lever 2700.

A cam mechanism coupled to the mounting block 2506 is used to lock the probe assembly 2502 to the electric meniscal sculptor 1500. The cam lever 2700 is used to operate the cam mechanism. With the cam lever 2700 in a downward position, as shown in FIG. 27, the cam mechanism locks the probe assembly 2502 to the device main body 2510. When the cam lever 2700 is rotated upward, the cam mechanism unlocks and the probe assembly 2502 may be removed from the device.

Figure 28:
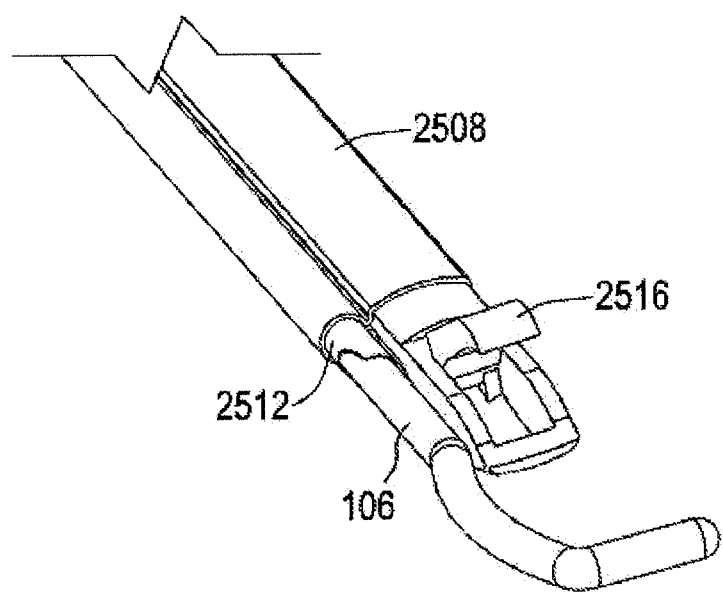
FIG. 28 is a partial front perspective view of the probe assembly installed on the biter device.

Referring next to FIG. 28, a partial front perspective view of the probe assembly 2502 installed on the biter device 2500 is shown. Shown are the probe 106, the sleeve 2508, the metal sleeve 2512, and the biter 2516.

As shown in FIG. 28, when the probe assembly 2502 is installed on the biter device 2500, the hook end of the probe 106 is proximate to the biter 2516. The probe 106 is shown in the retracted position but may be extended using the handle 2504.

While the invention herein disclosed has been described by means of specific embodiments, examples and applications thereof, numerous modifications and variations could be made thereto by those skilled in the art without departing from the scope of the invention set forth in the claims.

What is claimed is:

1. A device comprising:
a housing having a first housing end and a second housing end;
a pair of jaws including a biting surface, the pair of jaws located proximate to the second housing end and coupled to the housing such that the pair of jaws is pivotable relative to one another into an open position to receive a tissue between the pair of jaws and a closed position to cut the tissue between the pair of jaws; and
said pair of jaws further comprising: a first jaw; a second jaw; and a hinge point between said first jaw and said second jaw, wherein said pair of jaws is rotatable relative to one another about the hinge point to said open position and said closed position; and
an extendable probe coupled to the housing, the extendable probe is configured to be independently moved relative to the pair of jaws to pull the tissue into a position between the pair of jaws to be received by the pair of jaws in the open position; and
wherein said extendable probe is configured to pull the tissue toward the hinge point.

2. The device of claim 1 further comprising:
the extendable probe comprising a distal end, wherein the distal end comprises a bent end.

3. The device of claim 2 further comprising:
the extendable probe comprising the distal end, wherein the distal end comprises the bent end, wherein the bent end comprises a hook.

4. The device of claim 2 further comprising:
the extendable probe comprising an elastic material that can elastically bend sharply with an ability to return to an original linear configuration, wherein the elastic material bends into the bent end when the extendable probe is in an extended position.

5. The device of claim 2 further comprising:
the extendable probe comprising said distal end, wherein said distal end moves away from said pair of jaws as said extendable probe extends, and said distal end moves toward said pair of jaws as said extendable probe retracts.

6. The device of claim 5 further comprising:
the extendable probe comprising a portion of the extendable probe housed within the housing.

7. The device of claim 6 further comprising:
the extendable probe comprising the portion, wherein the portion ends at the second housing end.

8. The device of claim 6 further comprising:
the extendable probe comprising the portion, wherein the portion is between the first housing end and the second housing end.

9. The device of claim 1 further comprising:
said pair of jaws comprising:
a stationary upper jaw including the biting surface and located proximate to the second housing end, and
a moveable lower jaw, wherein the stationary upper jaw and the moveable lower jaw form a cutting mechanism with inner cutting surfaces.

10. The device of claim 1 further comprising:
said pair of jaws comprising:
a stationary lower jaw including the biting surface and located proximate to the second housing end, and
a moveable upper jaw, wherein the moveable upper jaw and the stationary lower jaw form a cutting mechanism with inner cutting surfaces.

11. The device of claim 1 further comprising:
said extendable probe comprising a distal end, wherein the distal end comprises a hook, and a portion of the extendable probe proximate to the hook is bent in an arcuate shape.

12. The device of claim 1, further comprising:
said extendable probe comprising a telescoping assembly.

13. The device of claim 1, further comprising:
the extendable probe comprising a distal end, wherein the distal end comprises a bent end, wherein said bent end is rotatable relative to said pair of jaws.

14. The device of claim 1 further comprising: said pair of jaws comprising: said first jaw comprising a rectangular shape; and said second jaw comprising U shape.

15. The device of claim 14 further comprising:
said pair of jaws comprising:
said hinge point proximate legs of the U shape.

16. The device of claim 14 further comprising:
said extendable probe, wherein said extendable probe extends through one of the legs of the U shape.

17. The device of claim 14 further comprising:
said extendable probe, wherein said extendable probe extends parallel to one of the legs of the U shape.

* * * * *